United States Patent
Lee et al.

(10) Patent No.: US 9,565,827 B2
(45) Date of Patent: Feb. 14, 2017

(54) ***BRASSICA CAMPESTRIS* VAR. *PEKINENSIS HONGBAECHOO* AS A NEW VARIETY OF PLANT AND A METHOD FOR BREEDING THE SAME**

(75) Inventors: Kwan Ho Lee, Suwon-si (KR); Yeong Hoe Woo, Incheon (KR); Gyu Hyeon Hong, Suwon-si (KR); Gyu Seon Seo, Suwon-si (KR); Woon Yong Lee, Suwon-si (KR)

(73) Assignee: Kwan Ho Lee, Seoul (KR)

( * ) Notice: Subject to any disclaimer, the term of this patent is extended or adjusted under 35 U.S.C. 154(b) by 365 days.

(21) Appl. No.: 13/993,672

(22) PCT Filed: Dec. 13, 2011

(86) PCT No.: PCT/KR2011/009590
§ 371 (c)(1),
(2), (4) Date: Jun. 12, 2013

(87) PCT Pub. No.: WO2012/081890
PCT Pub. Date: Jun. 21, 2012

(65) Prior Publication Data
US 2014/0013458 A1    Jan. 9, 2014

(30) Foreign Application Priority Data

Dec. 14, 2010  (KR) .................. 10-2010-0127366

(51) Int. Cl.
*A01H 5/12*    (2006.01)
*A01H 5/10*    (2006.01)

(52) U.S. Cl.
CPC . *A01H 5/12* (2013.01); *A01H 5/10* (2013.01)

(58) Field of Classification Search
None
See application file for complete search history.

(56) References Cited

PUBLICATIONS

Lee, Hwan Ho, "A New Brassica Species with 2n-40 Derived by Aneuploidy Breeding form B, campestris x B, oleracea in Brassica Crops," The Journal of Agriculture Education and Human Resource Development, 2001, vol. 33, No. 2, pp. 69-82.

*Primary Examiner* — Elizabeth McElwain
(74) *Attorney, Agent, or Firm* — Joseph Hyosuk Kim; JHK Law

(57) ABSTRACT

The present invention relates to methods of breeding *Brassica campestris* var. *pekinensis Hongbaechoo* grown by deriving interspecific hybrids with Hongssamchoo using Korean Cabbages as breeding plants and executing line acclimation test, self-incompatibility test and seed productivity test and reproduced by asexual propagation through tissue culturing method.

1 Claim, 5 Drawing Sheets

FIG 1

Year 1999    Korean Cabbage × Hongssamchoo

Year 2000    F1 Plant(line and individual selection)

Year 2001    F2 Plant × Korean Cabbage(line and individual selection)

Year 2002    B1F1 Plant × Korean Cabbage(line and individual selection)

Year 2003    B2F2 Plant(line cultivation, property test, productivity test)(line and individual selection)

Year 2004    B2F3 Plant(line cultivation, property test, productivity test, seed production test)(line and individual selection)

Year 2005    B2F4 Plant(line cultivation, property test, productivity test, seed production test)(line and individual selection)

Year 2006    B2F5 Plant(line cultivation, property test, productivity test, seed production test)(line and individual selection)

Year 2007    B2F6 Plant(line cultivation, property test, productivity test, seed production test,

Fig 1 (continued)

```
                 regional adaptation test)(line and individual selection)

Year 2008        B2F7 Plant(line cultivation, property test, productivity test, seed production test)(line and individual selection)

Year 2009        B2F8 Plant(line cultivation, property test, productivity test, seed production test)(line and individual selection)

Year 2010        B2F8 Plant ----- "Hongbaechoo"
```

BRASSICA CAMPESTRIS VAR. PEKINENSIS HONGBAECHOO AS A NEW VARIETY OF PLANT AND A METHOD FOR BREEDING THE SAME

TECHNICAL FIELD

The present invention relates to *Brassica campestris* var. *pekinensis Hongbaechoo* as a new variety of plant and a method for breeding the same by deriving interspecific hybrids with Hongssamchoo using Korean Cabbages as breeding plants and executing line acclimation test, self-incompatibility test and seed productivity test.

BACKGROUND ART

Korean Cabbages are one of most important vegetables in Korea in viewpoints of their history, acreage under cultivation, and usage. Korean Cabbages are a sort of green vegetables with phychrophilic properties. At a low temperature, flower buds of Korean Cabbages are differentiated and undergo anthesis and fructification. Korean Cabbages have seed vernalization types and are roughly classified into; heading breed, semiheading breed and no heading breed according to their heading shapes. The place of origin of Korean Cabbages is the north of China. The period of the introduction of Korean Cabbages into Korea is not clearly known, however considering the fact that Korean Cabbages were recorded in "Emergency Remedies using Country-bred Herbage" published in Year 23 of Emperor Gojong, Goryeo (Korean Dynasty) (1236 A.D.), Korean Cabbages are presumed to have been cultured before this publication.

When Korean Cabbages are cultivated for 60~80 days, they will have 40~90 leaves and become fully marketable if conditions for growth are met. Korean Cabbages are the most widely used vegetables in Korea as a main ingredient of Kimchi in Korea. Korean Cabbages have very high water content and substantial amount of calcium and vitamin C, and are source of fibroid material. Korean Cabbages can be eaten all the year round but in winter when frost forms, their fibroid material will be softened and flavor of Korean Cabbages will be intensified so Korean Cabbages become tasty all the more. Korean Cabbages can be stored easily. In winter season Korean Cabbages can be preserved for two or three weeks by erecting them at a cool place after wrapping them with old newspapers. In summer, Korean Cabbages are stored in a refrigerator after wrapping with wrappers. Korean Cabbages are appropriate vegetables for various recipes such as pot stews, fries, parboiled dishes, simmered dishes, kimchi, etc.

Cultivation styles of Korean Cabbages can be mainly divided into springtime seeding cultivation, high altitude cool region cultivation, Thanks-giving day Korean Cabbages cultivation, kimchi-making Korean Cabbages cultivation, winterization Korean Cabbages cultivation, and house cultivation. After germination, when the temperature becomes below 12℃ of low temperature, bolting (stalking) is activated. If a floral axis is formed, raceme develops. The flower is yellow and there are four stamens around one pistil. Korean Cabbages can be crossed easily since it has a distinct self-incompatibility, which is used for gathering seeds of F1 hybrid. Korean Cabbages are sensitive to high temperature, so it is difficult to culture Korean Cabbages in the middle of the summer. When the temperature exceeds 21~22℃, growth rate will be decreased and if heading starts at high temperature period, bacterial soft rot prevails, which is difficult to control.

Therefore researchers in the present invention have continued the research to develop new varieties of Korean Cabbages that may be used for rice wrapping vegetable, green vegetable juice and salad as well as kimchi, using such Korean Cabbages as breed breeding plants, and in consequence, the present invention was completed with the success of breeding *Brassica campestris* var. *pekinensis Hongbaechoo* by deriving interspecific hybrids between Korean Cabbages and Hongssamchoo and executing line acclimation test, self-incompatibility test and seed productivity test.

DISCLOSURE

Technical Problem

Accordingly, an object of the present invention relates to provide new varieties of plants that may be used for rice wrapping vegetable, green vegetable juice and salad as well as kimchi, using Korean Cabbages as breeding plants.

Another object of the present invention relates to providing methods of breeding new varieties of plants.

Technical Solution

In order to achieve the objects of the present invention, *Brassica campestris* var. *pekinensis Hongbaechoo* grown by deriving interspecific hybrids with Hongssamchoo using Korean Cabbages as breeding plants and executing line acclimation test, self-incompatibility test and seed productivity test and reproduced by unsexual propagation is provided, wherein;

(1) Leaves have somewhat oval and round shape;

(2) Inner side and outer side of a midrib represent white color, pink color or red color for individual plant, respectively;

(3) Heading types are circular shape and ellipsis shape;

(4) Front side and rear side of lamina(chlorophyll) are dyed red in scarlet color, and sometimes purple color or black color may be represented;

(5) The majority of veins show white color, and some veins represent pink color or red color;

(6) Leaf margin has a few flat jogs and bends showing pink color or red color;

(7) Size of heading is about ⅓ to ¼ of common Korean Cabbages;

(8) Phylloplane is glossy and mesophyll is crispy;

(9) The degree of self-incompatibility is low. Seed vernalization types are found as in radishes and Korean Cabbages; and

(10) This vegetable may be used for kimchi, rice wrapping vegetable, green vegetable juice or salad.

In order to achieve different purposes aforesaid, methods of breeding *Brassica campestris* var. *pekinensis Hongbaechoo* grown by deriving interspecific hybrids with Hongssamchoo using Korean Cabbages as breeding plants and executing line acclimation test, self-incompatibility test and seed productivity test are suggested.

Advantageous Effect

'*Pekinensis Hongbaechoo*' as a new variety of plant bred according to the present invention using Korean Cabbages as breeding plants may be used for rice wrapping vegetable, green vegetable juice and salad as well as kimchi as existing Korean Cabbages, and moreover, since its inner leaves represent beautiful reddish color, this vegetable would be highly useful in the industry thanks to its importance in agricultural economy.

DESCRIPTION OF DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein:

FIG. 1 is a breeding genealogical chart showing the process until 'Pekinensis Hongbaechoo' as a new variety of plant of the present invention could be obtained by collecting Korean Cabbages from 1999 to 2010;

DETAILED DESCRIPTION OF THE PREFERRED EMBODIMENTS

Figure 2:
FIG. 2 is a perspective view of 'Pekinensis Hongbaechoo' as a new variety of plant of the present invention.

The technical and scientific terms used in the present invention shall be interpreted to having ordinary meanings understood by a person who has ordinary skill in the art to which the present invention pertains unless other definitions are not given to them.

*Brassica campestris* var. *pekinensis* Hongbaechoo of the present invention was grown by deriving interspecific hybrids with Hongssamchoo using Korean Cabbages as breeding plants and executing line acclimation test, self-incompatibility test and seed productivity test and this vegetable may be reproduced by seed propagation using the above breeding methods or by asexual propagation through tissue culture.

*Pekinensis Hongbaechoo* of the present invention has the following properties;

(1) Leaves have somewhat oval and round shape;

(2) Inner side and outer side of a midrib represent white color, pink color or red color for individual plant, respectively;

(3) Heading types are circular shape and ellipsis shape;

(4) Front side and rear side of lamina(chlorophyll) are dyed red in scarlet color, and sometimes purple color or black color may be represented;

(5) The majority of veins show white color, and some veins represent pink color or red color;

(6) Leaf margin has a few flat jogs and bends showing pink color or red color;

(7) Size of heading is about ⅓ to ¼ of common Korean Cabbages;

(8) Phylloplane is glossy and mesophyll is crispy;

(9) The degree of self-incompatibility is low. Seed vernalization types are shown as in radishes and Korean Cabbages; and

(10) This vegetable may be used for kimchi, rice wrapping vegetable, green vegetable juice or salad.

Hongssamchoo used in the present invention is developed under Korean Patent Registration No. 10-0876970 which is a prior patent case registered by the inventor; the plant is *Brassica koreana* Lee var. redleaf by mating Korean Cabbages "Pyungchong No. 1" as mother with Korean Cabbages "Byung-gogye" as father to obtain one plant with 2n=40 of chromosome, mating Korean Cabbages "Byung-gogye" as mother with Korean Cabbages "Pyungchong No. 1" as father to obtain another plant 2n=40 of chromosome, mating those plants obtained to get seed parent, irradiating radioactive rays, line acclimating and sowing immediately after fruitage wherein:

1. Leaves

Morphology: somewhat oval and round shape.

Petiole: inner side of petiole is depressed and outer side of petiole being protruded representing reddish color.

Lamina: front side and rear side of lamina being dyed red in scarlet color, and sometimes purple color or black color being represented.

Veins: having more conspicuous red color than flat portion.

Margin: having a few flat jogs and bends showing red color.

Phylloplane: glossy.

2. Self-incompatibility: weak

3. Seed Vernalization Type

'*Pekinensis Hongbaechoo*' as a new variety of plant bred according to the present invention using Korean Cabbages as breeding plants may be used for rice wrapping vegetable, green vegetable juice and salad as well as kimchi as existing Korean Cabbages, and moreover, since its inner leaves represent beautiful reddish color, this vegetable would be highly useful in the industry thanks to its importance in agricultural economy. Hereunder, the present invention will be explained more specifically. However, the present invention may be implemented in various and different forms and not limited to the embodiments described here.

Embodiment 1

Breeding of a New Variety of Plant of the Present Invention

This embodiment is an experiment executed from year 1999 until year 2010 when a new variety of plant of the present invention was obtained by collecting Korean Cabbages. In FIG. 1, a genealogical chart of '*Pekinensis Hongbaechoo*' of the present invention is illustrated.

1) 1999-2002: Stabilization of hybrid Korean Cabbages was planned by collecting Korean Cabbages (Line Numbers B55, B57 B58, B9104, B9129) as material for breeding a new breed and deriving an interspecific hybrid (F1) of Korean Cabbages and Hongssamchoo developed by the inventor, and several lines of plants representing pink color, red color, etc. having shapes of existing Korean Cabbages were obtained through backcrossing to F2 plants using Korean Cabbages provided in above.

2) 2002-2010: 'Pekinensis Hongbaechoo' as a new variety of plant was obtained by conducting seed harvest test and regional adaptation test at the same time while executing line acclimation test, self-incompatibility test and seed productivity test annually on various lines of plants representing pink color, red color, etc. in shapes of existing Korean Cabbages. In the following Table 1, a breeding genealogical chart of breeding plants is shown.

(1) Leaves having somewhat oval and round shape;

(2) Inner side and outer side of a midrib representing white color, pink color or red color for individual plant, respectively;

(3) Heading types being circular shape and ellipsis shape;

(4) Front side and rear side of lamina(chlorophyll) being dyed red in scarlet color, and sometimes purple color or black color being represented;

TABLE 1

| Year | '99 | '00 | '01 | '02 | '03 | '04 | '05 | '06 | '07 | '08 | '09 | '10 |
|---|---|---|---|---|---|---|---|---|---|---|---|---|
| Data Collection | ──▶ | | | | | | | | | | | |
| Line Acclimation | | | ─────────────────────────────▶ | | | | | | | | | |
| Incompatibility Test | | | | | ─────────────────────▶ | | | | | | | |
| Combining Design | | ──────▶ | | | | | | | | | | |
| Combining Ability Test and Selection | | | ─────────────────────────────▶ | | | | | | | | | |
| Productivity Test | | | | | ─────────────────────▶ | | | | | | | |
| Seed Harvest Test | | ──────────────▶ | | | | | | | | | | |
| Regional Adaptation Connecting Test | | ──────▶ | | | | | | | | | | |

Embodiment 2

Cultivation of a New Variety of Plant of the Present Invention

A new variety of plant of the present invention "Pekinensis Hongbaechoo" obtained in the Embodiment 1 was cultivated according to common Korean Cabbages cultivation method.

Conditions of cultivation are as the follows: This vegetable is same species as common Korean Cabbages but "Pekinensis Hongbaechoo" has a high heat resistance and relatively low growth rate. Since its cultivation period is longer than common Korean Cabbages by 7~15 days and requires heavy dressing, this vegetable shall be cultivated by increasing the amount of fertilizers such as nitrogen, calcium, boron, etc.

Embodiment 3

Properties of a New Variety of Plant of the Present Invention

Figure 3:
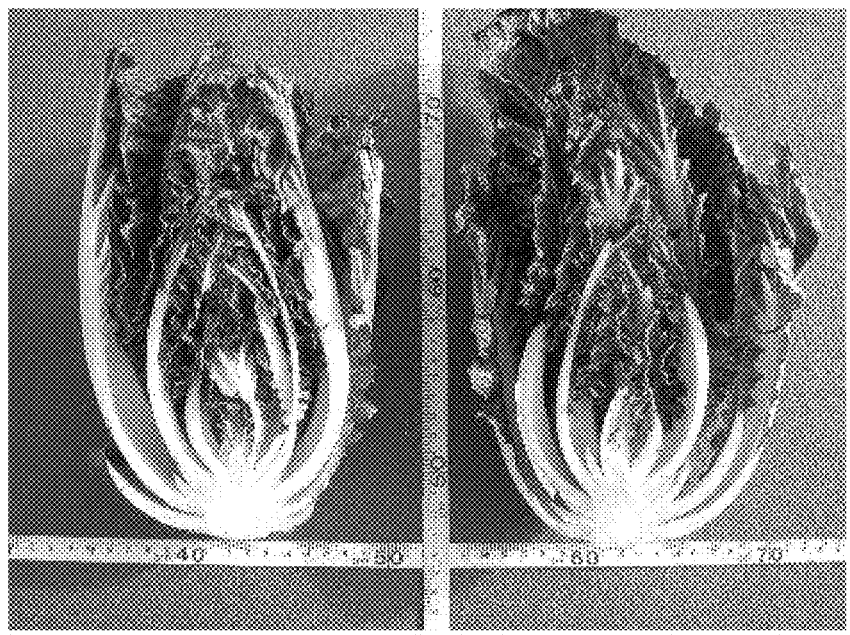
FIGS. 3 to 4 are cross sectional views of 'Pekinensis Hongbaechoo' as a new variety of plant of the present invention.
Figure 4:
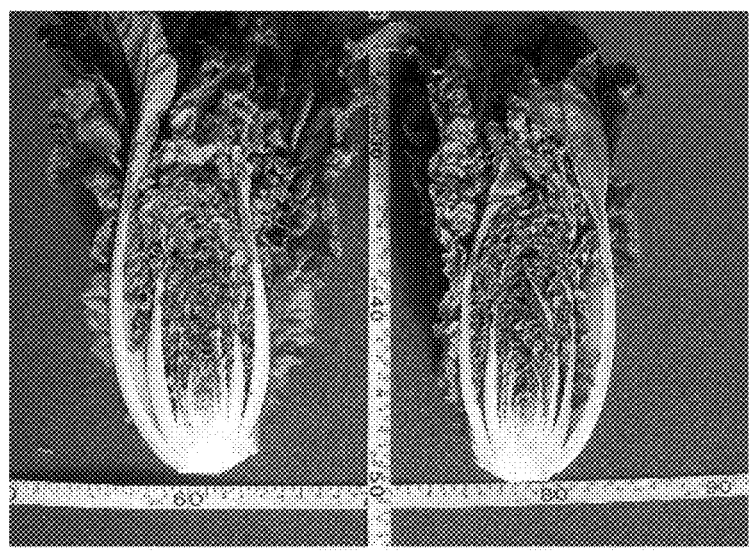

As shown in FIGS. 2 to 4, properties of a new variety of plant of the present invention "Pekinensis Hongbaechoo" are as follows:

(5) The majority of veins showing white color, and some veins represent pink color or red color;

(6) Leaf margin having a few flat jogs and bends showing pink color or red color;

(7) Size of heading being about ⅓ to ¼ of common Korean Cabbages;

(8) Phylloplane being glossy and mesophyll is crispy;

(9) The degree of self-incompatibility being low. Seed vernalization types being shown as in radishes and Korean Cabbages; and

(10) This vegetable being used for kimchi, rice wrapping vegetable, green vegetable juice or salad.

Embodiment 4

Comparison of 'Pekinensis Hongbaechoo' as a New Variety of Plant of the Present Invention and Korean Cabbages The results of the comparison of Pekinensis Hongbaechoo as a new variety of plant of the present invention and Korean Cabbages are shown in the following Table 2.

TABLE 2

| No | Properties | Phenotypes | | | | | | | | | (Pekinensis Hongbaechoo) No | (Korean Cabbages) No |
|---|---|---|---|---|---|---|---|---|---|---|---|---|
| | | 1 | 2 | 3 | 4 | 5 | 6 | 7 | 8 | 9 | | |
| 1 | Outer Leaf: Shape | Stand upright | Almost upright | Horizontal | | | | | | | 2 | 3 |
| 2 | Plant: Height | | | Small | | Middle | | Tall | | | 3 | 6 |
| 3 | Outer Leaf: Length | | | Short | | Middle | | Long | | | 3 | 5 |
| 4 | Outer Leaf: Width | | | Narrow | | Middle | | Wide | | | 5 | 3 |
| 5 | Outer Leaf: Width | Round | Broad egg | Upended egg | Narrow egg | Longish ellipsis | | | | | 1 | 3 |
| 6 | Outer Leaf: Foreend | Stumpy shape | Round shape | Flat shape | | | | | | | 2 | 3 |
| 7 | Outer Leaf: Jog | | | Mild | | Middle | | Severe | | | 5 | 5 |
| 8 | Outer Leaf: Size of Jog | | | Small | | Middle | | Big | | | 3 | 5 |
| 9 | Outer Leaf: Color | Scarlet | Yellowish green | Green | Gray green | | | | | | 1 | 3 |
| 10 | Outer Leaf: Intensity of Color | | | Light | | Middle | | Deep | | | 7 | 1 |
| 11 | Outer Leaf: Antocyanine pigment | Exists | | | | | | | | None | 9 | 1 |
| 12 | Outer Leaf: Gloss | | | Mild | | Middle | | Intense | | | 7 | 3 |
| 13 | Outer Leaf (Petiole): Lobation | None | | A few | | Middle | | Abundant | | Plentiful | 7 | 5 |
| 14 | Midrib | Wide | | Middle | | Narrow | | | | | 3 | 1 |
| 15 | Heading: Size | Small | | Middle | | Big | | | | | 1 | 5 |
| 16 | Heading: Weight | Light | | Middle | | Heavy | | | | | 1 | 5 |

Embodiment 5

Tissue Culturing of a New Variety of Plant of the Present Invention

The method of tissue culture executed in the present invention is to sow seeds of 'Pekinensis Hongbaechoo' in MS basal medium (plant growth regulator free) and differentiate it in a medium prepared with MS basal medium+NAA (Auxins)+BA (Cytokinins) using seed leaves with a bit of hypocotyl after one week. At this time, a medium added with 1-2 mg/mL of NAA and 6-8 mg/mL of BA was used.

INDUSTRIAL USABILITY

'Pekinensis Hongbaechoo' as a new variety of plant bred according to the present invention using Korean Cabbages as breeding plants may be used for rice wrapping vegetable, green vegetable juice and salad as well as kimchi as existing Korean Cabbages, and moreover, since its inner leaves represent beautiful reddish color, this vegetable would be highly useful in the industry thanks to its importance in agricultural economy.

The invention claimed is:
1. A *Brassica campestris* var. *pekinensis* Hongbaechoo grown from seed having Deposit Access No. KCTC 12410BP.

* * * * *